(12) United States Patent
Smith et al.

(10) Patent No.: US 12,091,373 B2
(45) Date of Patent: Sep. 17, 2024

(54) SYSTEMS AND PROCESSES FOR CATALYTIC CONVERSION OF $C_1$–$C_5$ ALCOHOLS TO $C_2$–$C_5$ OLEFIN MIXTURES

(71) Applicant: Gevo, Inc., Englewood, CO (US)

(72) Inventors: Jonathan Smith, Highlands Ranch, CO (US); Andrew Ingram, Denver, CO (US)

(73) Assignee: Gevo, Inc., Englewood, CO (US)

( * ) Notice: Subject to any disclaimer, the term of this patent is extended or adjusted under 35 U.S.C. 154(b) by 0 days.

(21) Appl. No.: 17/975,461

(22) Filed: Oct. 27, 2022

(65) Prior Publication Data

US 2023/0065667 A1 Mar. 2, 2023

Related U.S. Application Data

(63) Continuation-in-part of application No. PCT/US2022/026042, filed on Apr. 22, 2022.

(60) Provisional application No. 63/316,246, filed on Mar. 3, 2022, provisional application No. 63/219,803, filed on Jul. 8, 2021, provisional application No. 63/179,145, filed on Apr. 23, 2021.

(51) Int. Cl.
*C07C 1/24* (2006.01)

(52) U.S. Cl.
CPC ............ *C07C 1/24* (2013.01); *C07C 2529/06* (2013.01)

(58) Field of Classification Search
CPC .................................. C07C 1/20; C07C 1/22
See application file for complete search history.

(56) References Cited

U.S. PATENT DOCUMENTS

| 4,049,573 A * | 9/1977 | Kaeding .................. B01J 29/40 502/77 |
| 4,302,357 A | 11/1981 | Kojima et al. |
| 4,590,320 A | 5/1986 | Sapre |
| 8,378,136 B2 | 2/2013 | Dubois |
| (Continued) | | |

FOREIGN PATENT DOCUMENTS

| CN | 101172920 A | 5/2008 |
| CN | 101304963 A | 11/2008 |
| (Continued) | | |

OTHER PUBLICATIONS

International Search Report and Written Opinion received for PCT Application No. PCT/US2022/026042, mailed on Nov. 3, 2022, 20 Pages.

(Continued)

*Primary Examiner* — Sharon Pregler
(74) *Attorney, Agent, or Firm* — Mintz, Levin, Cohn, Ferris, Glovsky and Popeo, P.C.

(57) ABSTRACT

Processes for converting one or more $C_1$-$C_5$ linear or branched alcohols to one or more $C_2$-$C_5$ olefins are provided. In one exemplary embodiment, the process can be a single stage process for the direct conversion of $C_1$-$C_5$ alcohols to olefinic mixtures (e.g., $C_2$-$C_5$) carried out in a reactor using a catalyst that includes zeolite doped with boron and phosphor. Systems for carrying out these processes are also provided.

16 Claims, 4 Drawing Sheets

(56) References Cited

U.S. PATENT DOCUMENTS

| | | |
|---|---|---|
| 8,450,543 B2 | 5/2013 | Peters et al. |
| 8,552,241 B2 | 10/2013 | Coupard et al. |
| 9,840,676 B1 | 12/2017 | Harvey |
| 10,201,806 B2 * | 2/2019 | Braunsmann ........ B01J 37/0236 |
| 2011/0213174 A1 | 9/2011 | Dubois |
| 2016/0310934 A1 * | 10/2016 | Braunsmann ............ B01J 37/08 |
| 2017/0137357 A1 | 5/2017 | Hu et al. |
| 2022/0227685 A1 * | 7/2022 | Smith .................... B01J 21/066 |
| 2023/0065667 A1 * | 3/2023 | Smith ....................... C07C 1/20 |

FOREIGN PATENT DOCUMENTS

| | | | |
|---|---|---|---|
| CN | 102770397 A | 11/2012 | |
| CN | 102906053 A | 1/2013 | |
| CN | 103140458 A | 6/2013 | |
| CN | 103274884 A | 9/2013 | |
| CN | 107312569 A | 11/2017 | |
| EP | 2374780 A1 | 10/2011 | |
| EP | 2547639 B1 | 8/2016 | |
| WO | WO-2006036293 A1 * | 4/2006 | ............... C07C 1/00 |
| WO | 2010097175 A1 | 9/2010 | |
| WO | 2011085223 A1 | 7/2011 | |
| WO | 2011113834 A1 | 9/2011 | |
| WO | 2011113836 A1 | 9/2011 | |
| WO | 2011161045 A1 | 12/2011 | |
| WO | 2015088707 A1 | 6/2015 | |
| WO | 2018071905 A1 | 4/2018 | |
| WO | 2019136283 A1 | 7/2019 | |
| WO | 2021067294 A1 | 4/2021 | |
| WO | 2022226371 A2 | 10/2022 | |

OTHER PUBLICATIONS

Strizhak et al. (Nov. 15, 2017) "Methanol Conversion to Olefins on H-ZSM-5/Al2O3 Catalysts: Kinetic Modeling", Reaction Kinetics, Mechanisms and Catalysis, 123(1):247-268.

International Search Report And Written Opinion For PCT Patent Application No. PCT/US2020/053312, mailed on Jan. 6, 2021, 12 pages.

Invitation to Pay Additional Fees received for Application No. PCT/US2022/026042, mailed on Aug. 5, 2022, 11 pages.

Sadeghpour et al. (Sep. 15, 2018) "High-Temperature Efficient Isomorphous Substitution Of Boron Into 32,64 Zsm-5 Nanostructure For Selective And Stable Production Of Ethylene And Propylene From Methanol", Materials Chemistry and Physics, 217(1): 133-150(18 pages).

* cited by examiner

SYSTEMS AND PROCESSES FOR CATALYTIC CONVERSION OF $C_1$—$C_5$ ALCOHOLS TO $C_2$—$C_5$ OLEFIN MIXTURES

CROSS REFERENCE TO RELATED APPLICATIONS

This application is a continuation-in-part of International Patent Application No. PCT/US2022/026042 with an International Filing Date of Apr. 22, 2022, and entitled "Systems and Processes for Catalytic Conversion of $C_1$-$C_5$ Alcohols to $C_2$-$C_5$ Olefin Mixtures," which claims priority to U.S. Provisional Patent Application Nos. 63/179,145 filed on Apr. 23, 2021, and entitled "Single Step Conversion of C1-C2 Alcohols to Olefins," 63/219,803 filed on Jul. 8, 2021, and entitled "Single Step Conversion of C1-C2 bio-based or petro-based alcohols and mixtures thereof to C2-C7 olefins," and 63/316,246 filed on Mar. 3, 2022, and entitled "C2-C5 Olefin Recycle," which are hereby incorporated by reference in their entirety and for all purposes.

TECHNICAL FIELD

Systems and processes for catalytic conversion of $C_1$-$C_5$ alcohols, and more specifically, to catalytic processes resulting in the direct conversion of bio-based $C_1$-$C_5$ alcohols to olefinic mixtures ($C_2$-$C_5$) are provided.

BACKGROUND

There is an increasing demand for the use of biomass for partly replacing petroleum resources for the synthesis of fuels. The use of bioethanol for the synthesis of base stocks for fuels is therefore of great interest. The reaction at the root of the process of converting ethanol to a base stock for fuels is ethanol dehydration followed by ethylene oligomerization.

In most ethanol dehydration processes; ethanol conversion is nearly complete. The increase of $C_2$-selectivity while keeping high ethanol conversion is of importance to gain in process efficiency and to save expensive steps of downstream separation/purification. It is well known that dehydration occurs readily on acid solids at temperatures above 300° C. The reaction products are mainly water and ethylene, ethylene being obtained with selectivity's as high as 96+%. The most commonly used catalysts are high purity gamma aluminas, silica-aluminas, unprocessed zeolites (ZSM-5) or zeolites modified by steaming. Additionally, the presence of water in the ethanol feed would also have the effect of limiting catalyst surface deactivation.

U.S. Pat. No. 4,302,357 relates to an activated alumina catalyst employed in a process for production of ethylene from ethanol through a dehydration reaction. In the description LHSV of ethanol is from 0.25 to 5 h$^{-1}$ and preferably from 0.5 to 3 h$^{-1}$. The examples are carried out at 370° C. and LHSV of 1 h$^{-1}$, ethylene yield is from 65 to 94%. Process Economics Reviews PEP 79-3 (SRI international) of December 1979 describes the dehydration of an ethanol water (95/5 weight %) mixture on a silica-alumina catalyst in a tubular fixed bed at 315° C.-360° C., 1.7 bar absolute and a WHSV (on ethanol) of 0.3 h. The ethanol conversion is 99% and the ethylene selectivity is 94.95%. It also describes the dehydration of an ethanol-water (9575 weight %) mixture on a silica-alumina catalyst in a fluidized bed at 399° C., 1.7 bar absolute and a WHSV (on ethanol) of 0.7 h$^{-1}$. The ethanol conversion is 99.6% and the ethylene selectivity is 99.3%.

The oligomerization of ethylene requires high pressures, generally ranging between 2-4 MPa, but lower temperatures, generally between 20° C.-200° C. The catalysts used are in most cases transition metals deposited on silica-alumina type supports, zeolites (ZSM-5) or mesoporous solids (MCM-41) described by V. Hulea et al., J. Catal., 225 (2004) and Heveling et al., J. Applied Catalysis A: General 174 (1998). However, the direct oligomerization of ethylene results in relatively low amounts (~40% highest reported level) of $C_{10+}$ or diesel fraction. Alternatively, the oligomerization of ethylene to $C_{8+}$ olefins may be accomplished via a two-stage process. The first stage encompasses dimerization of a purified ethylene stream to butenes, followed by second stage oligomerization of butenes to $C_{8+}$ olefins which provides the base stock for fuels after hydrogenation.

U.S. Pat. No. 8,552,241 relates to a process for converting ethanol in a single step to a diesel fuel base stock which includes contacting ethanol with an acid catalyst at a reaction temperature of 300° C.-500° C. The catalyst used is a 50/50 mixture of a γ-alumina in combination with a commercial Axens catalyst "type IS463" marketed as an alumina-based catalyst for skeletal isomerization of $C_4$ and $C_5$ olefin cuts. The typical single pass product distribution consisted of a hydrocarbon fraction of 40-50%, and an organic liquid phase yield of 5-20%. The organic liquid phase consists of ~50% olefins of which $C_6$ olefins are the majority, and ~40% has a boiling point above 150° C., and therefore compatible with the diesel pool. The 40-50% hydrocarbon gaseous phase predominately contains ethylene and ethane as well as traces of $C_1$, $C_3$, $C_4$ and $C_5$. In this case, the yield to the organic liquid phase is relatively low with ~20% having a boiling point above 150° C. The other 80% of the organic liquid and hydrocarbon fraction is a predominately ethylene and ethane as well as traces of $C_1$, $C_3$, $C_4$ and $C_5$ and $C_6$ olefins.

U.S. Pat. No. 9,840,676 relates to a process for converting ethanol in a three-step process into fuels which can be utilized as full performance or military jet or diesel fuels. However, the process begins with ethylene formation followed by trimerization to hexenes and finally oligomerization to jet and diesel fractions.

Accordingly, there remains a needs for improved, efficient, and cost effective catalytic processes resulting in the direct conversion of bio-based alcohols to olefinic mixtures.

SUMMARY

Aspects of the current subject matter relate inter alia to systems and processes for converting one or more $C_1$-$C_5$ linear or branched alcohols to one or more $C_2$-$C_5$ olefins.

In one exemplary embodiment, process for converting one or more C1-C5 linear or branched alcohols to one or more C2-C5 olefins includes contacting an input stream comprising the one or more C1-C5 linear or branched alcohols with at least a first catalyst and a second catalyst in a single bed reactor to form an output stream. The output stream including the one or more C2-C5 olefins. The single bed reactor being at a temperature from about 350° C. to about 750° C., a gauge pressure from 0 to about 30 bar, and a weight hourly space velocity (WHSV) from about 0.5 to about 5.0. The first catalyst being a doped or undoped alumina catalyst including, in neutral or ionic form, one or more of zirconium (Zr), titanium (Ti), tungsten (W), or silicon (Si), to form a first mixture, and the second catalyst being a doped or undoped zeolite catalyst.

In some embodiments, the single bed reactor can be a fixed bed reactor. In other embodiments, the single bed reactor can be a fluidized bed reactor.

In some embodiments, contacting the input stream can further include contacting the input stream with a third catalyst in the single bed reactor. The third catalyst can include a doped or undoped $SiO_2$ catalyst.

In some embodiments, the $C_1$-$C_5$ linear or branched alcohols can be bio-based and produced by fermentative processes. In some embodiments, the $C_1$-$C_5$ linear or branched alcohols can be not derived from petroleum.

In some embodiments, the one or more $C_2$-$C_5$ olefins can be present in the output stream in an amount that can be at least 80 wt. %, at least 85 wt. %, at least 90 wt. %, or at least 95 wt. %.

In some embodiments, the output stream can include one or more aromatic ($C_{7+}$) compounds in an amount from about 2 wt. % to about 10 wt. %. In some embodiments, the output stream can include one or more aromatic ($C_{7+}$) compounds in an amount that does not exceed 10 wt. %.

In some embodiments, the process can include removing at least a portion of $C_2$ olefins from the output stream. In some embodiments, the process can include removing at least a portion of $C_4$ olefins from the output stream. In some embodiments, the process can include removing at least a portion of $C_5$ olefins from the output stream.

In some embodiments, the temperature can be from about 550° C. to about 750° C. In some embodiments, the temperature can be from about 350° C. to about 550° C.

In some embodiments, the WHSV can be from about 0.5 to about 1.0. In some embodiments, the WHSV can be from about 2.0 to about 5.0.

In another exemplary embodiment, a process for converting methanol to one or more $C_2$-$C_5$ olefins includes contacting an input stream comprising the methanol with at least a first catalyst and a second catalyst in a single bed reactor to form an output stream. The output stream including the one or more $C_2$-$C_5$ olefins. The single bed reactor being at a temperature from about 350° C. to about 750° C., a gauge pressure from 0 to about 30 bar, and a weight hourly space velocity (WHSV) from about 0.5 to about 5.0. The first catalyst being a doped or undoped alumina catalyst including, in neutral or ionic form, one or more of zirconium (Zr), titanium (Ti), tungsten (W), or silicon (Si), and the second catalyst being a doped or undoped zeolite catalyst.

In some embodiments, the single bed reactor can be a fixed bed reactor. In other embodiments, the single bed reactor can be a fluidized bed reactor.

In some embodiments, contacting the input stream can further include contacting the input stream with a third catalyst in the single bed reactor. The third catalyst can include a doped or undoped $SiO_2$ catalyst.

In some embodiments, the $C_1$-$C_5$ linear or branched alcohols can be bio-based and produced by fermentative processes. In some embodiments, the $C_1$-$C_5$ linear or branched alcohols can be not derived from petroleum.

In some embodiments, the one or more $C_2$-$C_5$ olefins can be present in the output stream in an amount that can be at least 80 wt. %, at least 85 wt. %, at least 90 wt. %, or at least 95 wt. %.

In some embodiments, the output stream can include one or more aromatic ($C_{7+}$) compounds in an amount from about 2 wt. % to about 10 wt. %. In some embodiments, the output stream can include one or more aromatic ($C_{7+}$) compounds in an amount that does not exceed 10 wt. %.

In some embodiments, the process can include removing at least a portion of $C_2$ olefins from the output stream. In some embodiments, the process can include removing at least a portion of $C_4$ olefins from the output stream. In some embodiments, the process can include removing at least a portion of $C_5$ olefins from the output stream.

In some embodiments, the temperature can be from about 550° C. to about 750° C. In some embodiments, the temperature can be from about 350° C. to about 550° C.

In some embodiments, the WHSV can be from about 0.5 to about 1.0. In some embodiments, the WHSV can be from about 2.0 to about 5.0.

In another exemplary embodiment, a process for converting one or more $C_1$-$C_5$ linear or branched alcohols to one or more $C_2$-$C_5$ olefins includes contacting an input stream that includes the one or more $C_1$-$C_5$ linear or branched alcohols with a first catalyst in a stacked bed reactor at a temperature from about 350° C. to about 550° C., a gauge pressure from 0 to about 30 bar, and a weight hourly space velocity (WHSV) from about 1.0 to about 2.0 to form a first mixture. The first catalyst being a doped or undoped alumina catalyst including, in neutral or ionic form, one or more of zirconium (Zr), titanium (Ti), tungsten (W), or silicon (Si). The process further including contacting the first mixture with at least a second catalyst in the stacked bed reactor to form an output stream that includes the one or more $C_2$-$C_5$ olefins, in which the second catalyst is a doped or undoped zeolite catalyst.

In some embodiments, the stacked bed reactor can be a fixed bed reactor. In other embodiments, the stacked bed reactor can be a fluidized bed reactor.

In some embodiments, contacting the first mixture can further include contacting the first mixture with a third catalyst in the stacked bed reactor. The third catalyst can include a doped or undoped $SiO_2$ catalyst.

In some embodiments, the $C_1$-$C_5$ linear or branched alcohols can be bio-based and produced by fermentative processes. In some embodiments, the $C_1$-$C_5$ linear or branched alcohols can be not derived from petroleum.

In some embodiments, the one or more $C_2$-$C_5$ olefins can be present in the output stream in an amount that can be at least 80 wt. %, at least 85 wt. %, at least 90 wt. %, or at least 95 wt. %.

In some embodiments, the output stream can include one or more aromatic ($C_{7+}$) compounds in an amount from about 2 wt. % to about 10 wt. %. In some embodiments, the output stream can include one or more aromatic ($C_{7+}$) compounds in an amount that does not exceed 10 wt. %.

In some embodiments, the process can include removing at least a portion of $C_2$ olefins from the output stream. In some embodiments, the process can include removing at least a portion of $C_4$ olefins from the output stream. In some embodiments, the process can include removing at least a portion of $C_5$ olefins from the output stream.

In some embodiments, the temperature can be from about 550° C. to about 750° C. In some embodiments, the temperature can be from about 350° C. to about 550° C.

In some embodiments, the WHSV can be from about 0.5 to about 1.0. In some embodiments, the WHSV can be from about 2.0 to about 5.0.

In another exemplary embodiment, a process for converting methanol to one or more $C_2$-$C_5$ olefins includes contacting an input stream that includes the methanol with a first catalyst in a stacked bed reactor at a temperature from about 350° C. to about 550° C., a gauge pressure from 0 to about 30 bar, and a weight hourly space velocity (WHSV) from about 1.0 to about 2.0 to form a first mixture. The first catalyst comprises a doped or undoped alumina catalyst including, in neutral or ionic form, one or more of zirconium (Zr), titanium (Ti), tungsten (W), or silicon (Si). The process further including contacting the first mixture with at least a second catalyst in the stacked bed reactor to form an output stream that includes the one or more $C_2$-$C_5$ olefins, in which the second catalyst is a doped or undoped zeolite catalyst.

In some embodiments, the stacked bed reactor can be a fixed bed reactor. In other embodiments, the stacked bed reactor can be a fluidized bed reactor.

In some embodiments, contacting the first mixture can further include contacting the first mixture with a third catalyst in the stacked bed reactor. The third catalyst can include a doped or undoped $SiO_2$ catalyst.

In some embodiments, the $C_1$-$C_5$ linear or branched alcohols can be bio-based and produced by fermentative processes. In some embodiments, the $C_1$-$C_5$ linear or branched alcohols can be not derived from petroleum.

In some embodiments, the one or more $C_2$-$C_5$ olefins can be present in the output stream in an amount that can be at least 80 wt. %, at least 85 wt. %, at least 90 wt. %, or at least 95 wt. %.

In some embodiments, the output stream can include one or more aromatic ($C_{7+}$) compounds in an amount from about 2 wt. % to about 10 wt. %. In some embodiments, the output stream can include one or more aromatic ($C_{7+}$) compounds in an amount that does not exceed 10 wt. %.

In some embodiments, the process can include removing at least a portion of $C_2$ olefins from the output stream. In some embodiments, the process can include removing at least a portion of $C_4$ olefins from the output stream. In some embodiments, the process can include removing at least a portion of $C_5$ olefins from the output stream.

In some embodiments, the temperature can be from about 550° C. to about 750° C. In some embodiments, the temperature can be from about 350° C. to about 550° C.

In some embodiments, the WHSV can be from about 0.5 to about 1.0. In some embodiments, the WHSV can be from about 2.0 to about 5.0.

In another exemplary embodiment, a process for converting one or more $C_1$-$C_5$ linear or branched alcohols to one or more $C_2$-$C_5$ olefins using a single catalyst system can include contacting an input stream that includes the one or more $C_1$-$C_5$ linear or branched alcohols with a catalyst in a reactor to form an output stream comprising the one or more $C_2$-$C_5$ olefins, in which the catalyst consists essentially of zeolite doped with boron and phosphor. The reactor is at a temperature from about 300° C. to about 600° C., a gauge pressure from 0 to about 30 bar, and a weight hourly space velocity (WHSV) from about 0.25 to about 10.

In some embodiments, the reactor can be a single bed reactor. In some embodiments, the single bed reactor can be a fixed bed reactor. In some embodiments, the single bed reactor can be a fluidized bed reactor. In some embodiments, the single bed reactor can be a moving bed reactor.

In some embodiments, the one or more $C_2$-$C_5$ olefins can be present in the output stream in an amount that is from about 50 wt. % to about 99 wt. % of the total hydrocarbon products in the output stream. In some embodiments, the one or more $C_2$-$C_5$ olefins can be present in the output stream in an amount that is from about 85 wt. % to about 99 wt. % of the total hydrocarbon products in the output stream.

In some embodiments, the boron can be present in the catalyst in an amount from about 0.01 wt. % to about 10 wt. %. In some embodiments, the boron can be present in the catalyst in an amount of at least 0.05 wt. %.

In some embodiments, the phosphor can be present in the catalyst in an amount from about 0.1 wt. % to about 7 wt. %. In some embodiments, the phosphor can be present in the catalyst in an amount of at least 1.5 wt. %.

In some embodiments, the zeolite can be ZSM-5 zeolite.

In another exemplary embodiment, a process for converting one or more $C_1$-$C_5$ linear or branched alcohols to one or more $C_2$-$C_5$ olefins using a single catalyst system can include contacting an input stream that includes the one or more $C_1$-$C_5$ linear or branched alcohols with a single catalyst in a reactor to form an output stream that includes the one or more $C_2$-$C_5$ olefins. The single catalyst includes zeolite doped with boron and phosphor. The reactor is at a temperature from about 350° C. to about 750° C., a gauge pressure from 0 to about 30 bar, and a weight hourly space velocity (WHSV) from about 0.25 to about 5.

In some embodiments, the single catalyst can consist essentially of zeolite doped with boron and phosphor.

In some embodiments, the reactor can be a single bed reactor. In some embodiments, the single bed reactor can be a fixed bed reactor. In some embodiments, the single bed reactor can be a fluidized bed reactor. In some embodiments, the single bed reactor can be a moving bed reactor.

In some embodiments, the one or more $C_2$-$C_5$ olefins can be present in the output stream in an amount that is from about 50 wt. % to about 99 wt. % of the total hydrocarbon products in the output stream. In some embodiments, the one or more $C_2$-$C_5$ olefins can be present in the output stream in an amount that is from about 85 wt. % to about 99 wt. % of the total hydrocarbon products in the output stream.

In some embodiments, the boron can be present in the catalyst in an amount from about 0.01 wt. % to about 10 wt. %. In some embodiments, the boron can be present in the catalyst in an amount of at least 0.05 wt. %.

In some embodiments, the phosphor can be present in the catalyst in an amount from about 0.1 wt. % to about 7 wt. %. In some embodiments, the phosphor can be present in the catalyst in an amount of at least 1.5 wt. %.

In some embodiments, the zeolite can be a ZSM-5 zeolite.

In another exemplary embodiment, the process for converting one or more $C_1$-$C_5$ linear or branched alcohols to one or more $C_2$-$C_5$ olefins using a single catalyst system can include contacting an input stream that includes the one or more $C_1$-$C_5$ linear or branched alcohols with a catalyst in a reactor to form an output stream that includes the one or more $C_2$-$C_5$ olefins. The catalyst consists essentially of ZSM-5 zeolite doped with boron and phosphor. The reactor is at a temperature from about 350° C. to about 475° C., a gauge pressure from 0 to about 5 bar, and a weight hourly space velocity (WHSV) from about 0.25 to about 10. The boron is present in the catalyst in an amount from about 0.05 wt. % to about 5 wt. %, and the phosphor is present in the catalyst in an amount from about 0.2 wt. % to about 7 wt. %.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

DETAILED DESCRIPTION

Figure 1:
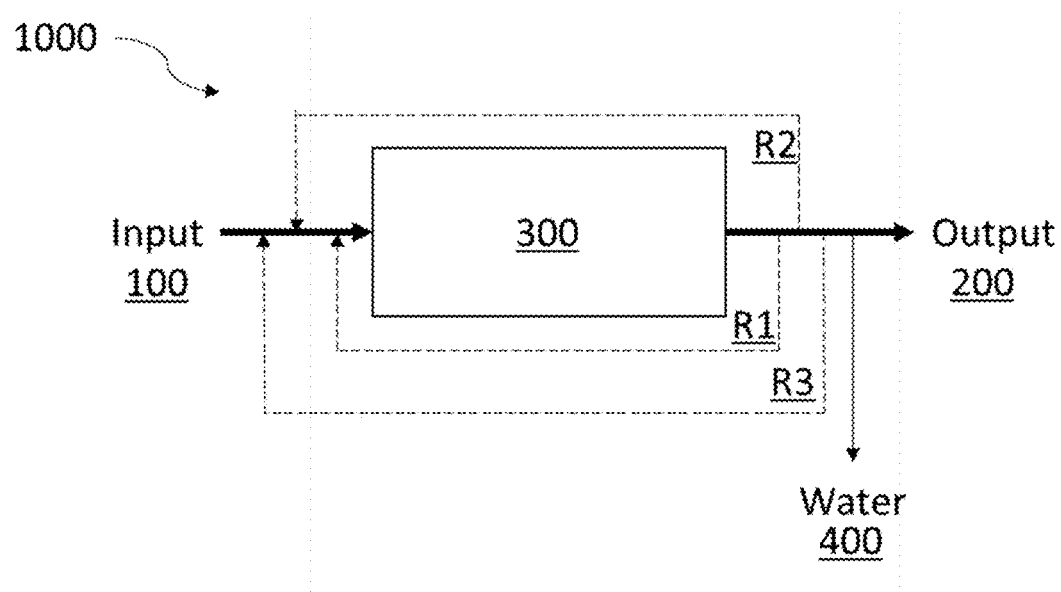
FIG. 1 shows an example process concept for an on-purpose propylene configuration of a single fixed bed reactor system with closed-loop recycle of $C_2$, $C_4$, and $C_5$ olefins, consistent with implementations of the current subject matter.

In the following description, certain specific details are set forth in order to provide a thorough understanding of various embodiments. However, one skilled in the art will understand that the disclosure may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed disclosure.

Reference throughout this specification to "one embodiment" or "an embodiment" means a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the context clearly dictates otherwise. It should also be noted that the term "or" is generally employed in its sense including "and/or" unless the context clearly dictates otherwise.

The word "about" when immediately preceding a numerical value means a range of plus or minus 10% of that value, e.g., "about 50" means 45 to 55, "about 25,000" means 22,500 to 27,500, etc. Furthermore, the phrases "less than about" a value or "greater than about" a value should be understood in view of the definition of the term "about" provided herein.

"Oxygenate" refers to compounds which include oxygen in their chemical structure. Examples of oxygenates include, but are not limited to water, alcohols, esters, and ethers.

"WHSV" refers to weight hourly space velocity and is defined as the weight of the feed flowing per unit weight of the catalyst per hour.

"Aromatics" or "aromatic compounds" as used herein refer to cyclic organic carbon compounds consisting of six or more carbons (e.g. benzene, etc.).

"Trace amounts" or "trace levels" as used herein refer to levels less than 2%. In some embodiments, trace amounts or trace levels can refer to levels less than about 1.5%, less than about 1%, less than about 0.5%, less than about 0.1%, from about 0.1% to about 1.8%, or from about 1% to about 1.5%.

"Single stage transformation" refers to processes which occur within a single reactor system.

All yields and conversions described herein are on a weight basis unless specified otherwise.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

As previously disclosed in WO 2021/067294, which is incorporated herein in its entirety, alcohols may be converted to an olefinic mixture including primarily $C_2$-$C_7$ olefins with low levels of aromatic compounds. The processes provide paths towards economical ways to convert alcohols, e.g. ethanol, to base stocks for the production of fuels. Further, the processes described herein can be performed at lower pressures and higher temperatures with higher yields of olefins in comparison to previously available approaches. The processes may include a single stage transformation of an aqueous bioalcohol feedstock derived from biomass into a higher molecular weight olefinic mixture, which can easily be oligomerized in high yield to $C_{10+}$ hydrocarbons or diesel fractions. The single-stage reactor or two-stage reactor configurations use specific catalytic systems, which make it possible to minimize the production of aromatic compounds and therefore maximize production of middle distillates. Processes described in WO 2021/067294 convert $C_2$-$C_5$ alcohols efficiently and economically as a base stock for fuels. Conversion of $C_2$-$C_5$ alcohols to the desired fuel product precursors (e.g., $C_3$-$C_7$ olefins) in high yields reduces processing costs.

Aspects of the subject matter disclosed herein improve on earlier approaches by, inter alia, providing processes in which a two-catalyst system is used to convert $C_2$-$C_5$ linear or branched alcohols to $C_2$-$C_7$ olefins in high yield with low levels of aromatics at competitive costs. Consistent with the current disclosure, processes for the direct conversion of bio-based $C_1$-$C_5$ alcohols to olefinic mixtures (e.g., $C_2$-$C_5$) with low levels of aromatics may be carried out in a single fixed bed reactor. The $C_2$-$C_5$ olefins can be easily oligomerized to base stocks used in the production of fuels in high yields.

In some embodiments, the processes described herein can be carried out in a single bed reactor. In other embodiments, the processes described herein can be carried out in a single stacked bed reactor. For example, in certain embodiments, alcohols, e.g. methanol or ethanol, may be converted to olefinic mixtures (e.g., $C_2$-$C_5$) in a single reactor having a first catalyst in the top section of the reactor with a second catalyst being located in a section of the reactor below the first catalyst. In either the single-stage processes (e.g., using a single bed reactor) or in the two-stage processes (e.g., using a stacked bed reactor), the resulting $C_2$-$C_5$ olefinic mixture is suitable for oligomerization into either gasoline, jet, or diesel fuel cuts at relatively low temperatures and pressures depending upon the oligomerization catalyst selected. Further, in some embodiments, the single bed reactor or stacked bed reactor can be defined as a fixed bed reactor, whereas in other embodiments, a fluidized bed reactor may be used.

Systems and processes for catalytic conversion of $C_1$-$C_5$ alcohols are provided. In general, a catalytic process consistent with the present disclosure includes alcohol dehydration followed by a skeletal carbon build-up and subsequent "cracking" resulting in high yields to low molecular weight olefins (e.g., $C_2$-$C_5$). In this single stage process, the catalyst mixture can result in a $C_2$-$C_5$ olefinic mixture providing access to low molecular weight olefins in yields with good carbon accountability as defined by moles of carbon fed into the system as ethanol versus moles of carbon out of the system incorporated in the $C_2$-$C_5$ olefinic mixture. Furthermore, use of recycle streams of specific olefins (e.g., $C_2$-$C_5$) advantageously results in the ability to maximize the on-purpose formation of desirable olefins such as propylene, butenes, or mixtures thereof. In some embodiments, the mixture of olefins are suitable for oligomerization to either gasoline, jet, or diesel fuel cuts at relatively low temperatures and pressures depending upon the oligomerization catalyst selected.

As stated previously, most $C_2$-$C_5$ alcohols are dehydrated in a single unit operation, at between 300° C.-500° C. in the presence of a dehydration catalyst, resulting in production of the $C_2$-$C_5$ olefin along with water. The water is removed, and the $C_2$-$C_5$ olefin is further processed/purified to remove unreacted $C_2$-$C_5$ alcohols and/or impurities prior to conversion to chemicals and/or fuels. Relative to ethanol ($C_2$ alcohol), the classical approach to conversion to chemicals and/or fuels utilizes discrete unit operations to accomplish i) dehydration to ethylene, ii) ethylene purification followed by dimerization to butenes, iii) cracking to propylene, iv) oligomerization of butenes to unsaturated Jet and/or Diesel fuel precursors, or v) direct oligomerization of ethylene to unsaturated Jet and/or Diesel fuel precursors. Similarly, the approach to converting $C_4$ or $C_5$ alcohols to chemicals and/or fuels utilize discrete unit operations to accomplish i) dehydration to the $C_4$ or $C_5$ olefin, ii) olefin purification to remove oxygenates and/or unreacted alcohols, and iii) oligomerization to unsaturated Jet and/or Diesel fuel precursors. Relative to methanol, industrial processes convert methanol, primarily derived from coal, to olefins via a mesoporous catalyst (e.g., SAPO-34, etc.) to olefins in a single step with olefin recycle.

A concept which simultaneously dehydrates, oligomerizes, and cracks $C_1$-$C_5$ alcohols or mixtures thereof in one reactor is challenging due to higher temperatures required for complete dehydration (e.g., from about 300° C. to about 500° C.), and large amounts of water present. Implementation of a single unit operation capable of simultaneously dehydrating, oligomerizing, and cracking olefins derived from $C_1$-$C_5$ alcohol dehydration requires that catalysts employed be able to withstand high temperatures along with large amounts of water and other oxygenates.

To address these challenges, and to define an approach to convert $C_1$-$C_5$ alcohols into a viable feedstock resulting in high yields to fuels, a process has been developed capable of converting $C_1$-$C_5$ alcohols, via a single unit operation (e.g., a single reactor), to a mixture of $C_2$-$C_5$ olefins in high yield, which is readily separable for use as chemical feedstocks or easily oligomerized to base stocks for fuels in high yield. The ability to accomplish numerous unit operations and chemical transformations in a single reactor, as presented herein, provides the practitioner with favorable economics due to reduced fixed and variable costs, lower capital investment, less energy, and increased productivity.

To this end, consistent with the current disclosure the conversion of methanol, and/or mixtures of methanol and $C_2$-$C_5$ alcohols, proceeds similarly to a $C_2$-$C_5$ olefin mixture in high yield and carbon accountability. An exemplary single reaction step encompasses i) dehydration, ii) oligomerization to $C_{4+}$ olefins, iii) skeletal rearrangement, and iv) cracking to primarily propylene along with minor amounts of $C_{4+}$ olefins and aromatics. Thus, passing a vaporized stream of methanol and ethanol over a single fixed catalyst bed containing a physical mixture of containing the first part of a silicated, zirconated, titanated, niobium, or fluorinated γ-alumina combined with a doped zeolite (boron, phosphor, or combinations thereof) as the second catalyst part at between about 300° C. to about 450° C. results in a $C_2$-$C_5$ olefin mixture, which can be separated for sale, or after removal of condensed water, oligomerized "as-is" to primarily jet and/or diesel fuel. This catalyst combination in a single fixed bed reactor accomplishes i) dehydration, ii) oligomerization to $C_{4+}$ olefins, iii) skeletal rearrangement, and iv) cracking that results in longer catalyst time on stream (ToS), improved hydrothermal stability, and improved selectivity to olefins with lesser amounts of saturates and aromatics.

Furthermore, the present systems and processes may optionally include the recycle of one or more specific olefin fractions (e.g., $C_2$+$C_4$+$C_5$ or $C_2$+$C_5$, etc.) in a closed-loop process configuration, while co-feeding the $C_1$-$C_5$ alcohols. This can result in the maximization of on-purpose yields to selected olefins. For example, the recycle of the $C_2$+$C_4$+$C_5$ olefin fraction in combination with co-feeding $C_1$-$C_5$ alcohols using the present system and processes provided herein unpredictably resulted in an on-purpose propylene carbon yield exceeding 80 wt. %. Selective recycle of the $C_2$+$C_5$ olefin fraction results in an on-purpose propylene and butenes combined carbon yield exceeding 80 wt. %. Example 8 gives more detail regarding the unpredictable yield achieved when using the recycle of specific olefin fractions described herein. Additionally, recycle of the $C_4$+$C_5$ olefin fraction can result in an on-purpose ethylene and propylene combined carbon yield exceeding 80 wt. %. An exemplary single-step reaction can encompass i) in-situ dehydration, ii) oligomerization to $C_{3+}$ olefins, iii) skeletal rearrangement, and iv) cracking to $C_2$-$C_5$ olefins along with formation of minor amounts of $C_{5+}$ olefins and aromatics. Recycling the olefin fraction of choice can therefore enable on-purpose olefin production for chemicals and/or fuels production.

Unlike conversion of ethylene, propylene and other olefins of higher molecular weight ($C_{4+}$) can easily be oligomerized over a wide range of catalysts of both zeolitic and non-zeolitic type. The present disclosure, enabling the ability to convert $C_1$-$C_5$ alcohols in a single stage, or two-stage reactor configuration in series, to an olefin mixture which includes of primarily $C_2$-$C_5$ olefins with low levels of aromatics, presents a path towards an economical process to convert $C_1$-$C_5$ alcohols to base stocks for chemicals and/or fuels. The process according to the invention implements a scheme that includes a "single" stage transformation of an aqueous $C_1$-$C_5$ bio-alcohols feedstock obtained from biomass into primarily $C_2$-$C_5$ olefinic mixture, which may be separated to isolate key low molecular weight olefins used throughout the industry as chemical building blocks, or may be easily oligomerized in high yield to $C_{10+}$ hydrocarbons or diesel fraction. The two stage or single stage configuration using specific catalytic systems makes it possible to minimize the production of aromatic compounds and therefore maximize production of middle distillates, which constitutes both an asset for the ethanol refiner and an advantage from the standpoint of lasting development.

International patent application WO 2010/097175A1 relates to the direct conversion of alcohols and oxygenates via a two-stage process in which both the first and second stage reactors in series have a commercially available type ZSM-5 zeolite catalyst added (Zeolyst CBV-28014). The first reactor is brought to a temperature of 460° C., and the temperature of the second reactor to 320° C. After temperatures have stabilized the feed consisting of 86% methanol, 9% isopropanol, and 5% water is initiated. Methanol single pass conversion is typically >95% and the reported final liquid product mainly consists of 60-85% $C_n$ olefins with n≥5, between 15-40% by weight of light $C_n$ olefins with n=2–4, and <10% aromatics. The final liquid product is preferably hydrogenated to give gasoline cuts, or oligomerized according to conventional processes to give mixtures of gasoline, kerosene, and diesel.

Conversion of $C_1$-$C_5$ alcohols to the desired fuel product, or fuel product precursors (e.g., $C_2$-$C_5$ olefins) as in the case of $C_1$-$C_5$ alcohols, or mixtures thereof, in a single fixed bed reactor configuration, can reduce processing costs. In one exemplary embodiment, a process for converting one or more $C_1$-$C_5$ linear or branched alcohols to one or more $C_2$-$C_5$ olefins is provided. The process includes: contacting an input stream comprising the one or more $C_1$-$C_5$ linear or branched alcohols with at least a first catalyst and a second catalyst in a single bed reactor to form an output stream comprising the one or more $C_2$-$C_5$ olefins, the single bed reactor being at a temperature from about 350° C. to about 750° C., a gauge pressure from 0 to about 30 bar, and a weight hourly space velocity (WHSV) of about 0.5 to about 5.0.

Exemplary catalyst combinations, physically mixed within the single-fixed bed reactor, for $C_2$-$C_5$ olefin formation can include one part (e.g., a first catalyst) doped zeolites such as crystalline silicates of the group ZSM-5 (MFI or BEA frameworks), CHA, FER, FAU, MWW, MOR, EUO, MFS, ZSM-48, MTT or TON having Si/Al higher than 10, or a dealuminated crystalline silicate of the group ZSMS (MFI or BEA frameworks), CHA, FER, FAU, MWW, MOR, EUO, MFS, ZSM-48, MTT or TON having Si/Al higher than 10, or a phosphorus and/or boron modified crystalline silicate of the group ZSM-5 (MFI or BEA frameworks), CHA, FER, FAU, MWW, MOR, EUO, MFS, ZSM-48, MTT or TON having Si/Al higher than 10, or molecular sieves of the type silico-aluminophosphate of the group AEL. Additional additives for mixing with doped zeolites consist of $SiO_2$ supports doped with metal dopants including iron (Fe), strontium (Sr), cobalt (Co), nickel (Ni), lanthanum (La), chromium (Cr), zirconium (Zr), ruthenium (Ru), molybdenum (Mo), iridium (Ir), magnesium (Mg), tungsten (W), copper (Cu), manganese (Mn), vanadium (V,) zinc (Zn), titanium (Ti), rhodium (Rh), rhenium (Re), gallium (Ga), palladium (Pd), silver (Ag), indium (In). A second part of the catalyst mixture (e.g., a second catalyst) can include a silicated, zirconated, titanated, niobium, or fluorinated γ-alumina. By way of example, the aforementioned exemplary catalyst combination efficiently dehydrates the $C_1$-$C_5$ alcohols to their respective olefins, while the doped zeolite results in the oligomerization and cracking to $C_2$-$C_5$ olefins with lesser amounts of saturates and aromatics in comparison to literature reports utilizing a single component zeolite catalyst or metal oxide catalyst.

The following representative example(s) relate to converting $C_1$-$C_5$ alcohols, or mixtures thereof, to primarily propylene and butenes in >85 wt. % carbon yields along with lesser amounts of $C_{5+}$ olefins and aromatics (BTX) via a single unit operation with quantitative $C_1$-$C_5$ alcohol conversion. Furthermore, desirable carbon accountability is achieved as further indicated by no detection of carbon monoxide or carbon dioxide along with trace amounts of methane. Unreacted olefin fractions (e.g., $C_2$-$C_5$ olefins) may be separated and recycled resulting in the on-purpose formation in high yield and carbon accountability to the desired olefin.

Granular or extruded catalyst(s) can be used for the reactions described herein. For example, in some embodiments, granular or extruded catalyst(s) can have a particle size of greater than at least about 0.05 mm, about 0.1 mm or greater, or from about 0.05 mm to about 2.5 mm, including all the subranges in between. In one embodiment, granular or extruded catalysts(s) can have a particle size from about 0.4 to about 2.0 mm.

This disclosure describes a process for converting one or more $C_1$-$C_5$ linear or branched alcohols to one or more $C_2$-$C_5$ olefins. In certain embodiments, the process includes: contacting an input stream that includes the one or more $C_1$-$C_5$ linear or branched alcohols with at least a first catalyst and a second catalyst in a single bed reactor to form an output stream that includes the one or more $C_2$-$C_5$ olefins, in which the single bed reactor is at a temperature from about 350° C. to about 750° C., a gauge pressure from 0 to about 30 bar, and a weight hourly space velocity (WHSV) from about 0.5 to about 5.0, where the first catalyst includes a doped or undoped alumina catalyst including, in neutral or ionic form, one or more of zirconium (Zr), titanium (Ti), tungsten (W), or silicon (Si); and the second catalyst includes a doped or undoped zeolite catalyst.

This disclosure also describes a process for converting methanol to one or more $C_2$-$C_5$ olefins. In certain embodiments, the process includes contacting an input stream that includes the methanol with at least a first catalyst and a second catalyst in a single bed reactor to form an output stream comprising the one or more $C_2$-$C_5$ olefins. The single bed reactor operates at a temperature from about 350° C. to about 750° C., a gauge pressure from 0 to about 30 bar, and a weight hourly space velocity (WHSV) from about 0.5 to about 5.0, and the first catalyst includes a doped or undoped alumina catalyst including, in neutral or ionic form, one or more of zirconium (Zr), titanium (Ti), tungsten (W), or silicon (Si). The second catalyst includes a doped or undoped zeolite catalyst.

This disclosure also provides a process for converting one or more $C_1$-$C_5$ linear or branched alcohols to one or more $C_2$-$C_5$ olefins. In certain embodiments, the process can include: contacting an input stream that includes the one or more $C_1$-$C_5$ linear or branched alcohols with a first catalyst in a stacked bed reactor to form an output stream that includes the one or more $C_2$-$C_5$ olefins. The stacked bed reactor is at a temperature from about 350° C. to about 550° C., a gauge pressure from 0 to about 30 bar, and a weight hourly space velocity (WHSV) from about 1.0 to about 2.0, and the first catalyst includes a doped or undoped alumina catalyst including, in neutral or ionic form, one or more of zirconium (Zr), titanium (Ti), tungsten (W), or silicon (Si). The process further includes contacting the first mixture with at least a second catalyst, where the second catalyst includes a doped or undoped zeolite catalyst.

This disclosure also provides a process for converting methanol to one or more $C_2$-$C_5$ olefins. In certain embodiments, the process includes contacting an input stream that includes the methanol with a first catalyst in a stacked bed reactor to form a first mixture. The stacked bed reactor is at a temperature from about 350° C. to about 550° C., a gauge pressure from 0 to about 30 bar, and a weight hourly space velocity (WHSV) from about 1.0 to about 2.0. The first catalyst includes a doped or undoped alumina catalyst including, in neutral or ionic form, one or more of zirconium (Zr), titanium (Ti), tungsten (W), or silicon (Si), to form a first mixture. The first mixture is then contacted with at least a second catalyst to form an output stream that includes the one or more $C_2$-$C_5$ olefins, and the second catalyst includes a doped or undoped zeolite catalyst.

In some embodiments of the subject matter, contacting the input stream or first mixture further includes contacting the input stream or first mixture with a third catalyst. The third catalyst may be a doped or undoped $SiO_2$ catalyst. The reactor may be a fixed bed reactor, and/or a fluidized bed reactor. Suitable $C_1$-$C_5$ linear or branched alcohols include those which are bio-based and produced by fermentative processes, and those which are not derived from petroleum.

Regarding the output stream, the $C_2$-$C_5$ olefins may be present in an amount that is at least 80 wt. % of the output stream. The $C_2$-$C_5$ olefins may be present in an amount from 80 wt. % 99 wt. %, including all the subranges in between, of the output stream The $C_2$-$C_5$ olefins may be present in an amount that is at least 85 wt. % of the output stream. The $C_2$-$C_5$ olefins may be present in an amount that is at least 90 wt. % of the output stream. The $C_2$-$C_5$ olefins may be present in an amount that is at least 95 wt. % weight percent. Further regarding the output stream, the processes disclosed herein may further include removing at least a portion of the $C_2$ olefins from the output stream. The processes may include removing at least a portion of the $C_4$ olefins from the output stream. The processes may include removing at least a portion of the $C_5$ olefins from the output stream.

Regarding the reactor, the reactor may be operated at a temperature from about 350° C. to about 550° C., including all the subranges in between. The reactor may be operated at a temperature from about 550° C. to about 750° C., including all the subranges in between. The reactor may be operated at a WHSV from about 0.5 to about 1.0, including all the subranges in between. The reactor may be operated at a WHSV from about 2.0 to about 5.0, including all the subranges in between. The reactor may be a fixed bed reactor. The reactor may be a fluidized bed reactor.

The disclosure also describes a process for converting one or more $C_1$-$C_5$ linear or branched alcohols to one or more $C_2$-$C_5$ olefins using a single catalyst system. In other words, these disclosed processes use a system having only one catalyst. The use of a single catalyst system can be desirable in a variety of instances, for example, when some portion of unconverted $C_1$-$C_5$ linear or branched alcohols and related oxygenates are acceptable in the output stream, or when the catalyst is continuously regenerated during operation, which can be implemented in, for example, fluidized bed or moving bed reactors. In some embodiments, the one or more $C_1$-$C_5$ linear or branched alcohols can be one or more $C_1$-$C_5$ linear or branched monohydric alcohols.

Conversion of $C_1$-$C_5$ alcohols to the desired fuel product, or fuel product precursors (e.g., $C_2$-$C_5$ olefins) as in the case of $C_1$-$C_5$ alcohols, or mixtures thereof with a single catalyst system can, for example, reduce processing costs and simplify and optimize the conversion process that would not otherwise be possible with a two-catalyst system. In these processes, the single catalyst system includes only one catalyst, such as doped zeolite. In some embodiments, the only one catalyst is not a doped or undoped alumina catalyst. In certain embodiments, the zeolite can be zeolite doped with boron and phosphor. Non-limited examples of zeolites olefin formation can include one part (e.g., a first catalyst) doped zeolites such as crystalline silicates of the group ZSM-5 (MFI or BEA frameworks), CHA, FER, FAU, MWW, MOR, EUO, MFS, ZSM-48, MTT or TON having Si/Al higher than 10, or a dealuminated crystalline silicate of the group ZSMS (MFI or BEA frameworks), CHA, FER, FAU, MWW, MOR, EUO, MFS, ZSM-48, MTT or TON having Si/Al higher than 10. In some embodiments, when the zeolite is a ZSM-5 zeolite, the ZSM-5 zeolite can have a $Si/Al_2O_3$ ratio from about 20 to about 300. In certain embodiments, the ZSM-5 zeolite can have a $Si/Al_2O_3$ ratio from about 50 to about 150.

In some embodiments, the single catalyst system includes only zeolite doped with boron and phosphor. Without being bound by a single theory, it is believed that the presence of boron increases the stability of the phosphor during time on stream (TOS), while also maintaining selectivity. That is, the presence of boron in such instances can minimize the production of saturates and aromatics in the output stream.

Boron and phosphor can be present within the single catalyst system at a variety of different concentrations. In some embodiments, the boron can be present in the single catalyst system in amount from about 0.01 wt. % to about 10 wt. %, including all the subranges in between. In certain embodiments, the boron can be present in the single catalyst system in an amount from about 0.05 wt. % to about 5 wt. %, including all the subranges in between. In certain embodiments, the boron can be present in the single catalyst system in an amount from about 0.05 wt. % to about 3 wt. %, including all the subranges in between. In one embodiment, the boron can be present in the single catalyst system in an amount of at least 0.05 wt. %. In some embodiments, the phosphor can be present in the single catalyst system in amount from about 0.1 wt. % to about 7 wt. %, including all the subranges in between. In certain embodiments, the phosphor can be present in the single catalyst system in an amount from about 1.5 wt. % to about 6 wt. %, including all the subranges in between. In one embodiment, the phosphor can be present in the single catalyst system in an amount of at least 3 wt. %. In certain embodiments, the boron can be present in the single catalyst system in amount from about 0.5 wt. % to about 3 wt. %, and the phosphor can be present in the single catalyst system in an amount from about 2 wt. % to 6 wt. %.

In one exemplary embodiment, a process for converting one or more $C_1$-$C_5$ linear or branched alcohols to one or more $C_2$-$C_5$ olefins using a single catalyst system can include contacting an input stream that includes the one or more $C_1$-$C_5$ linear or branched alcohols with a catalyst in a reactor to form an output stream comprising the one or more $C_2$-$C_5$ olefins, in which the catalyst consists essentially of zeolite doped with boron and phosphor. The reactor is at a temperature from about 300° C. to about 600° C., a gauge pressure from 0 to about 30 bar, and a weight hourly space velocity (WHSV) from about 0.25 to about 10.

In another exemplary embodiment, a process for converting one or more $C_1$-$C_5$ linear or branched alcohols to one or more $C_2$-$C_5$ olefins using a single catalyst system can include contacting an input stream that includes the one or more $C_1$-$C_5$ linear or branched alcohols with a single catalyst in a reactor to form an output stream that includes the one or more $C_2$-$C_5$ olefins. The single catalyst includes zeolite doped with boron and phosphor. The reactor is at a temperature from about 350° C. to about 750° C., a gauge pressure from 0 to about 30 bar, and a weight hourly space velocity (WHSV) from about 0.25 to about 5.0. in certain embodiments, the single catalyst consists essentially of zeolite doped with boron and phosphor.

In some embodiments, the process can include, after contacting the input stream with the catalyst in the reactor, regenerating the catalyst. In some embodiments, the regeneration of the catalyst can be carried out by purging any gaseous or liquid hydrocarbons or oxygenates from the reactor and then introducing air and/or oxygen optionally diluted with inert gas or steam to combust any solid carbon deposits on the catalyst. In some embodiments, the process can include, a system whereby the catalyst is circulated between a reactor in which it is contacted with the input stream and a regeneration reactor in which is it contacted with air and/or oxygen optionally diluted with inert gas or steam to combust any solid carbon deposits on the catalyst.

In some embodiments, the process can further include contacting another input stream that includes the one or more $C_1$-$C_5$ linear or branched alcohols with the regenerated catalyst (e.g., the catalyst post-regeneration) in the reactor to form another output stream comprising one or more $C_2$-$C_5$ olefins. A person skilled in the art will appreciate that the regenerated catalyst can have a lower concentration of boron, phosphor, or both compared to the catalyst prior to regeneration.

Regarding the reactor, the reactor can be operated at a temperature from about 300° C. to about 750° C., including all the subranges in between. The reactor can be operated at a temperature from about 350° C. to about 700° C., including all the subranges in between. The reactor can be operated at a temperature from about 300° C. to about 600° C. The reactor can be operated at a gauge pressure from 0 to about 30 bar, including all the subranges in between. The reactor can be operated at a gauge pressure from 0 to about 5 bar, including all the subranges in between. The reactor can be operated at a gauge pressure of about 6 or lower. The reactor can be operated at a WHSV from about 0.1 to about 10, including all the subranges in between. The reactor can be operated at a WHSV from about 0.25 to about 10, including all the subranges in between. The reactor can be operated at a WHSV from about 0.25 to about 5, including all the subranges in between. The reactor can be operated at a WHSV from about 1 to about 10, including all the subranges in between. The reactor can be a fixed bed reactor. The reactor can be a fluidized bed reactor. The reactor can be a moving bed reactor.

Regarding the output stream, the $C_2$-$C_5$ olefins can be present in the output stream in an amount that is at least 50 wt. % of the total hydrocarbon products in the output stream. The total hydrocarbon products in the output stream does include any water that can be present in the output stream. The $C_2$-$C_5$ olefins can be present in the output stream in an amount from about 50 wt. % to about 85 wt. %, including all the subranges in between, of the total hydrocarbon products in the output stream. The $C_2$-$C_5$ olefins can be present in the output stream in an amount from about 50 wt. % to about 99 wt. %, including all the subranges in between, of the total hydrocarbon products in the output stream. The $C_2$-$C_5$ olefins can be present in the output stream in an amount from about 70 wt. % to about 99 wt. %, including all the subranges in between, of the total hydrocarbon products in the output stream. The $C_2$-$C_5$ olefins can be present in the output stream in an amount from about 85% wt. to about 99 wt. %, including all the subranges in between, of the total hydrocarbon products in the output stream. The $C_2$-$C_5$ olefins can be present in the output stream in an amount that is at least 85 wt. % of the total hydrocarbon products in the output stream. The $C_2$-$C_5$ olefins can be present in the output stream in an amount that is at least 90 wt. % of the total hydrocarbon products in the output stream. The $C_2$-$C_5$ olefins can be present in the output stream in an amount that is at least 95 wt. % of the total hydrocarbon products in the output stream.

Further regarding the output stream, the processes disclosed herein can further include removing at least a portion of the $C_2$ olefins from the output stream. The processes can include removing at least a portion of the $C_3$ olefins from the output stream. The processes can include removing at least a portion of the $C_4$ olefins from the output stream. The processes can include removing at least a portion of the $C_5$ olefins from the output stream.

In one exemplary embodiment, a process for converting one or more $C_1$-$C_5$ linear or branched alcohols to one or more $C_2$-$C_5$ olefins using a single catalyst system can include contacting an input stream that includes the one or more $C_1$-$C_5$ linear or branched alcohols with a catalyst in a reactor to form an output stream that includes the one or more $C_2$-$C_5$ olefins. The catalyst consists essentially of ZSM-5 zeolite doped with boron and phosphor. The reactor is at a temperature from about 350° C. to about 475° C., a gauge pressure from 0 to about 5 bar, and a weight hourly space velocity (WHSV) from about 0.25 to about 10. The boron is present in the catalyst in an amount from about 0.05 wt. % to about 5 wt. %, and the phosphor is present in the catalyst in an amount from about 0.2 wt. % to about 7 wt. %.

The following specific examples are intended to be illustrative of the invention and should not be construed as limiting the scope of the invention as defined by appended claims.

The foregoing detailed description has been given for clearness of understanding only and no unnecessary limitations should be understood there from as modifications will be obvious to those skilled in the art.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

EXAMPLES

Example 1: Reactor Set-Up

Alcohol (i.e., $C_1$-$C_5$) conversion to $C_2$-$C_5$ olefins was carried out at 300° C.-500° C., via fixed bed reactors, containing specified catalyst(s), and flowing preheated (160° C.) vaporized alcohol in a downward flow over the fixed catalyst bed while co-feeding nitrogen at atmospheric pressure or under moderate pressures (i.e., 0-30 bar). The flow rate of alcohol was controlled by Teledyne Model 500D syringe pumps, and the flow rates were adjusted to obtain the targeted olefin WHSV (weight hourly space velocity). The internal reaction temperature was maintained constant via a Lindberg Blue M furnace as manufactured by Thermo-Scientific. Alcohol conversion and selectivity was calculated by analysis of the liquid phase reactor effluent by GC for organic and water content, online GC analysis of non-condensed hydrocarbons (i.e., $C_2$-$C_5$ olefins), and on-line thermal conductivity detector for quantitation of CO, $CO_2$ and $CH_4$ relative to nitrogen as internal standard. Thus, passing a vaporized stream of $C_1$-$C_5$ alcohols over the catalyst combination in a single fixed bed reactor at between 350° C.-450° C. results in the formation of $C_2$-$C_5$ olefins in high yields.

Example 2: Impregnated Zr-γ-Alumina (Nominal Zr Metal 5 wt %) Catalyst Preparation Zr-γ-Alumina catalyst was prepared by incipient wetness technique as described. The precursor metal salts (Sigma Aldrich): 2.64 g Zirconium (IV) oxynitrate hydrate was dissolved in deionized water (14.9 mL). Upon salt dissolution, the solution was added in dropwise fashion to 15 g γ-alumina support. The resulting mixed metal oxide was manually mixed to assure complete wetting, and the resulting impregnated catalyst was dried at 160° C. for 1 hr, and afterwards calcined at 500° C. for 4 hrs.

Example 3: Impregnated Boron/Phosphor Impregnated ZSM-5 Zeolite Catalyst Preparation Boron and Phosphor impregnated zeolite catalyst was prepared by incipient wetness technique as described. 0.78 g phosphoric acid (85%) and 0.96 g boric acid (99+%) was dissolved in deionized water (7.4 mL). Upon heating and dissolution, the solution was added in dropwise fashion to 6 g ZSM-5 zeolite support (i.e., Zeolyst type CBV-5524 $H^+$). The resulting impregnated catalyst was dried at 160° C. for 1 hr, and afterwards calcined at 550° C. for 3-15 hrs.

Example 4: Single Stage Reactor

Single Stage reactor configuration: Reaction Conditions: T=355° C. in reactor, WHSV=2.5 (methanol basis), P=0 bar; Catalysts-Zirconated (4.0 wt %) γ-Alumina physically mixed with doped ZSM-5 zeolite.

TABLE 1

Single pass reactor effluent composition and corresponding weight percent of total.

| Single Pass Reactor Effluent Composition | Wt % of Total: |
|---|---|
| Ethylene | 32 |
| Propylene | 20 |
| Butenes | 17 |
| $C_5$ olefins | 8 |
| $C_2$-$C_5$ saturates | 20 |
| Aromatics ($C_{7+}$) | 3 |
| $C_{6+}$ olefins | trace |

Ethylene conversion~68% mass yield.

Example 5: Single Stage Reactor

Single Stage reactor configuration: Reaction Conditions: T=425° C. in reactor, WHSV=4.5 (ethanol basis), P=0 bar; Catalysts-Zirconated (4.0 wt %) γ-Alumina physically mixed with doped ZSM-5 zeolite and Ni doped $SiO_2$.

TABLE 2

Single pass reactor effluent composition and corresponding weight percent of total.

| Single Pass Reactor Effluent Composition | Wt % of Total: |
|---|---|
| Ethylene | 37.5 |
| Propylene | 20.9 |
| Butenes | 18.7 |
| $C_5$ olefins | 9.7 |
| $C_2$-$C_5$ saturates | 11.2 |
| Aromatics ($C_{7+}$) | 2 |
| $C_{6+}$ olefins | trace |

Ethylene conversion~62% mass yield.

Example 6: Single Stage Reactor

Single Stage reactor configuration: Reaction Conditions: Feed pre-heater T=160° C., Reactor T=445° C., Total WHSV=3.4 (includes recycle), P=0-1 bar; Catalyst: Zirconated (4.0 wt %) γ-Alumina physically mixed with doped ZSM-5 zeolite; Feed Composition: hydrous ethanol (92%) =0.15 ml/min, ethylene recycle=70 ml/min (0.087 g/min); mixed butenes=23 ml/min (0.057 g/min), mixed pentenes=0.035 ml/min, nitrogen=10 ml/min.

TABLE 3

Single pass reactor effluent composition and corresponding weight percent of total.

| Reactor Effluent Composition | Wt % of Total: |
|---|---|
| ethylene | 33.6 |
| ethane | 0.6 |
| propylene | 23.9 |
| propane | 4.8 |
| isobutane | 3.2 |
| isobutylene | 6.9 |
| n-butene | 4.6 |
| n-butane | 1.7 |
| trans-2-butene | 4.5 |
| cis-2-butene | 3.36 |
| pentanes | 3.0 |
| pentenes | 8.6 |
| Aromatics ($C_{7+}$) | 2 |
| $C_{6+}$ olefins | trace |

TABLE 4

| Final Output. | |
|---|---|
| Component | Mass, kg/hr |
| Propane | 517 |
| Propylene | 3321 |
| Aromatics ($C_{7+}$) | 245 |
| Total | 4082 |

The process concept and mass balance for the on-purpose propylene (81% yield) configuration with closed-loop recycle of $C_2$, $C_4$, and $C_5$ olefins based on experimental data from Example 6 is depicted in FIG. 1. The recycling of $C_2$, $C_4$, and $C_5$ olefins maximizes on-target olefin formation. FIG. 1 shows a single stage reactor system 1000. As shown in the figure, an input 100, such as hydrous ethanol (92%) may be fed into a fixed bed reactor 300, to produce an output 200, such as a $C_2$-$C_5$ olefin mixture having the final output given in Table 4 above. Additionally, recycle streams R1, R2, and R3 may recycle $C_2$, $C_4$, and $C_5$ olefins respectively, back into the input 100 to be fed back into the fixed bed reactor 300. Wastewater 400 may also be produced in situ by the fixed bed reactor 300, via dehydration of ethanol to ethylene, and thus condensed and removed as part of the output 200.

Example 7: Simultaneous Dehydration, Dimerization, Skeletal Rearrangement, and Cracking of $C_1$-$C_5$ Bio-Based Der Petro-Based Alcohols and Mixtures Thereof to $C_2$-$C_7$ Olefins The purpose of this example is to provide data illustrating the conversion of $C_1$-$C_5$ bio-based or petro-based alcohols to $C_2$-$C_7$ olefinic mixtures, having low levels of aromatic compounds. Details of the reactor set up and resulting effluent stream, as well as yield data, are provided below.

Single Stage reactor configuration: Reaction Conditions: T=425° C. in reactor, WHSV=4.5 (ethanol basis), P=0 bar;

Catalysts-Zirconated (4.0 wt %) γ-Alumina physically mixed with doped ZSM-5 zeolite and Ni doped $SiO_2$.

TABLE 5

Single Pass Reactor Effluent Composition and Weight Percent of total.

| Single Pass Reactor Effluent Composition | Wt % of Total: |
|---|---|
| Ethylene | 37.5 |
| Propylene | 20.9 |
| Butenes | 18.7 |
| $C_5$ olefins | 9.7 |
| $C_2$-$C_5$ saturates | 11.2 |
| Aromatics | 2.0 |
| $C_{6+}$ olefins | trace |

Ethylene conversion~62% mass yield.

Example 8: Increased Propylene Yield Using Olefin Fraction Recycling

Provided herein are data illustrating the increased yield using $C_2$/$C_3$/$C_4$ olefin fraction recycling as disclosed herein.
Single Stage reactor configuration for data of Table 6: Reaction Conditions: Feed pre-heater T=160° C., Reactor T=445° C., Total WHSV=4.35, P=0-1 bar; Catalyst: Zirconated (4.0 wt %) γ-Alumina.

TABLE 6

Single pass yield of propylene without $C_2$/$C_3$/$C_4$ recycle.

| | | \multicolumn{4}{c}{Single Pass Yields (no recycle); JS-144a} | | | | |
|---|---|---|---|---|---|
| | | Mass In | Mass Out | Carbon in | Carbon out | % Carbon Yield |
| EtOH Feed, 92% | kg/hr | 7,290 | | 291.6 | | |
| Propane | kg/hr | | 79 | | 5.4 | 1.8% |
| Propylene | kg/hr | | 794 | | 56.7 | 19.4% |
| Water | kg/hr | | 3,208 | | — | |
| Ethylene | kg/hr | | 2,043 | | 145.9 | 50.0% |
| Ethane | kg/hr | | 18 | | 1.2 | 0.4% |
| iso-Butane | kg/hr | | 85 | | 5.9 | 2.0% |
| iso-Butylene | kg/hr | | 217 | | 15.5 | 5.3% |
| 1-Butene | kg/hr | | 145 | | 10.4 | 3.6% |
| n-Butane | kg/hr | | 33 | | 2.4 | 0.8% |
| t-2-Butene | kg/hr | | 139 | | 9.9 | 3.4% |
| c-2-Butene | kg/hr | | 102 | | 7.3 | 2.5% |
| pentenes | kg/hr | | 296 | | 21.1 | 7.3% |
| pentanes | kg/hr | | 45 | | 3.1 | 1.1% |
| Aromatics (C8) | kg/hr | | 82 | | 6.2 | 2.1% |
| | | | | | 291.0 | 100% |

Single Stage reactor configuration for data of Table 7: Reaction Conditions: Feed pre-heater T=160° C., Reactor T=445° C., Total WHSV=3.7 (includes recycle), P=0-1 bar; Catalyst: Zirconated (4.0 wt %) γ-Alumina.

TABLE 7

Max propylene yields with $C_2$/$C_3$/$C_4$ recycle.

| | | Max Propylene Mode Yields with C2/C3/C4 Recycle (closed Loop); MS-194b | | | | |
|---|---|---|---|---|---|---|
| | | Mass In | Mass Out | Carbon in | Carbon out | Carbon Yield |
| EtOH Feed, 92% | kg/hr | 7,290 | | 291.6 | | |

TABLE 7-continued

Max propylene yields with $C_2$/$C_3$/$C_4$ recycle.

| | | Max Propylene Mode Yields with C2/C3/C4 Recycle (closed Loop); MS-194b | | | | |
|---|---|---|---|---|---|---|
| | | Mass In | Mass Out | Carbon in | Carbon out | Carbon Yield |
| Propane | kg/hr | | 296 | | 20.2 | 6.9% |
| Propylene | kg/hr | | 2,997 | | 214.1 | 73.4% |
| Water | kg/hr | | 3,190 | | — | |
| Ethylene | kg/hr | | 31 | | 2.2 | 0.8% |
| Ethane | kg/hr | | 19 | | 1.3 | 0.4% |
| iso-Butane | kg/hr | | 117 | | 8.1 | 2.8% |
| Butenes | kg/hr | | 229 | | 16.4 | 5.6% |
| pentenes | kg/hr | | 138 | | 9.9 | 3.4% |
| pentanes | kg/hr | | 39 | | 2.7 | 0.9% |
| Aromatics (C8) | kg/hr | | 153 | | 11.5 | 4.0% |
| | | | | | 286.3 | 98% |

Example 9: Conversion of Ethanol Over Boron and Phosphor Doped Zeolite

Provided herein are data illustrating the usage of a boron and phosphorous doped zeolite for the conversion of alcohols to mixed olefins.

Single Stage Reaction Conditions: Feed pre-heater T=165° C., Reactor T=445° C., Total WHSV=3.53, P=0-1 bar; Catalyst: 5 gm of ZSM-5 zeolite (Si/$Al_2$=90) doped with 2 wt. % B, 3 wt. % P, Feed Composition: 0.3 mL/min 92% ethanol, 40 standard cubic centimeter per minute (SCCM) ethylene, 10 SCCM nitrogen. Table 7, provided below, lists the gaseous hydrocarbon products after 24 hr time on stream (TOS).

TABLE 7

Gaseous Hydrocarbon Products

| Gaseous Product | Wt % in dry gas |
|---|---|
| Ethylene | 40.21 |
| Ethane | 0.75 |
| Propylene | 19.27 |
| Propane | 4.63 |
| isobutane | 6.58 |
| isobutylene/1-butene | 9.61 |
| n-butane | 2.06 |
| trans-2-butene | 3.78 |
| cis-2-butene | 2.72 |
| 3-methyl-1-butene | 0.26 |
| isopentane | 2.58 |
| 1-pentene | 0.35 |
| 2-methyl-1-butene | 1.50 |
| pentane | 0.59 |
| trans-2-pentene | 1.11 |
| cis-2-pentene | 0.59 |
| 2-methyl-2-butene | 3.26 |

Figure 2:
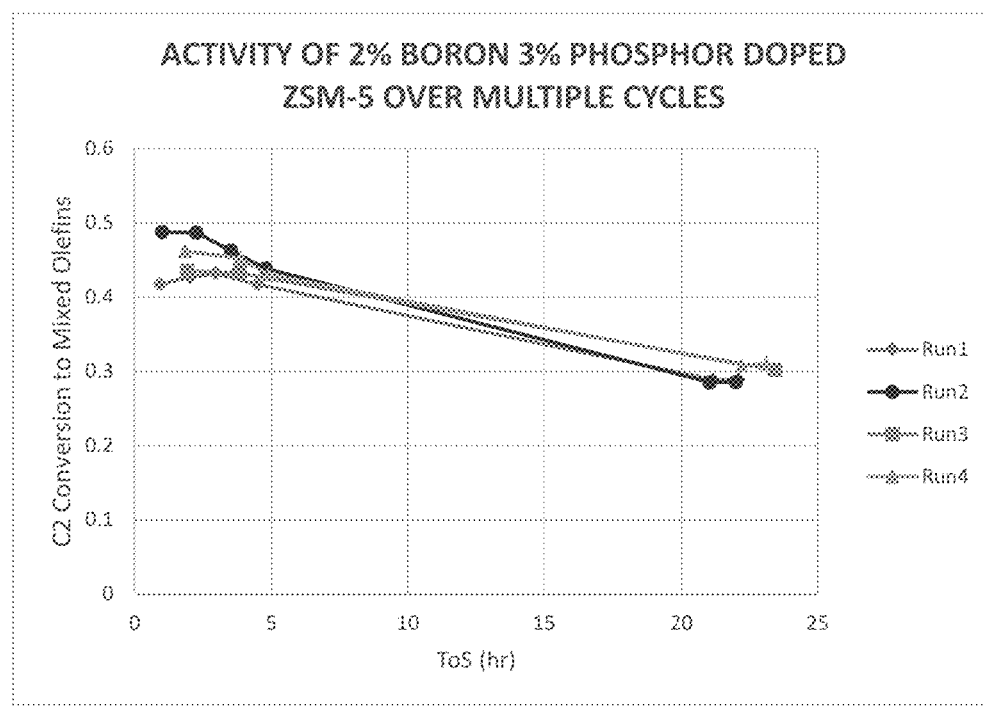
FIG. 2 is a graph illustrating the data results of Example 10.

Example 10: Repeated Use of Boron and Phosphor Doped Zeolite with Zr-Alumina Single Stage Reaction Conditions: Feed pre-heater T=165° C., Reactor T=445° C., P=0-1 bar; Admixed Catalyst: first part 2.5 gm of ZSM-5 zeolite (Si/$Al_2$=90) doped with 2% B, 3% P; second part 2.5 gm of γ-$Al_2O_3$ doped with 4% Zr; Feed: 0.35 mL/min 92% ethanol, 60 SCCM ethylene, 10 SCCM nitrogen. Regeneration Conditions: Removed admixed catalyst from reactor and placed in a static muffle furnace overnight at 500° C. Admixed catalyst was subjected to 24 hours time on stream, then repeatedly regenerated and resubjected to reaction conditions. The data shown in FIG. 2 illustrates the activity (e.g., $C_2$ conversion/gram/hour of the ZSM-5 zeolite ($Si/Al_2$=90) doped with of 2% B, 3% P (first part) is repeatable, and therefore can be substantially similar across multiple runs, which in this example are Runs 1-4.

Figure 3:
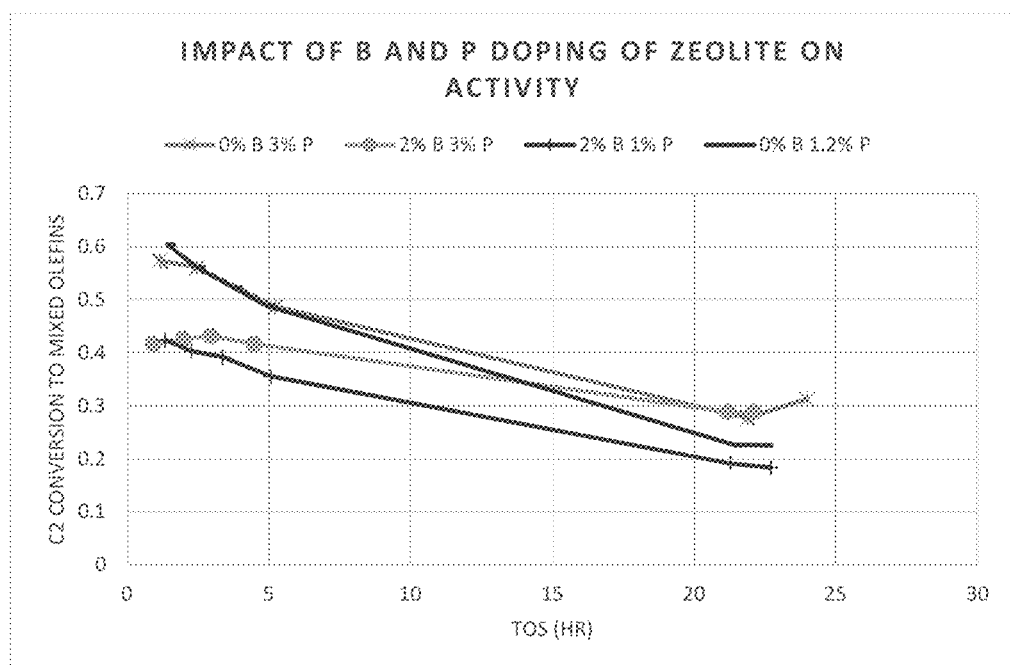
FIG. 3 is a graph illustrating the date results of Example 11.

Example 11: Impact of Boron and Phosphor Loading on Catalytic Activity and Stability Single Stage Reaction Conditions: Feed pre-heater T=165° C., Reactor T=445° C., P=0-1 bar; Admixed Catalyst: first part 2.5 gm of ZSM-5 zeolite ($Si/Al_2$=90) doped with of 2% B, 3% P; second part 2.5 gm of γ-$Al_2O_3$ doped with 4% Zr; Feed: 0.35 mL/min 92% ethanol, 60 SCCM ethylene, 10 SCCM nitrogen. Catalysts were subjected to 24 hours time on stream. The data shown in FIG. 3 illustrates ethylene conversion with varying boron and phosphor doping concentrations on ZSM-5 zeolite in accordance with this Example. As shown in FIG. 3, the exemplary catalyst with the highest doping concentration of boron and phosphor (i.e., 2% B and 3% P) shows the greatest stability compared to the other exemplary catalysts.

Example 12: Repeated Use of Phosphor Doped Zeolite with Zr-Alumina

Figure 4:
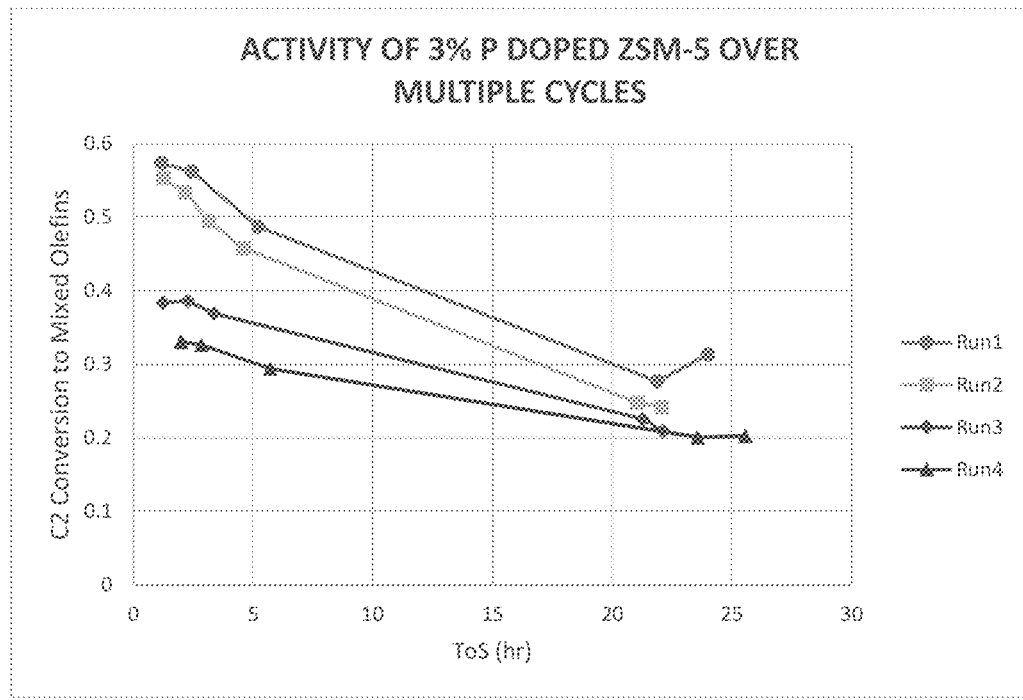
FIG. 4 is a graph illustrating the data results of Example 12.

This is a comparative example with respect to Example 10. Single Stage Reaction Conditions: Feed pre-heater T=165° C., Reactor T=445° C., P=0-1 bar; Admixed Catalyst: first part 2.5 gm of ZSM-5 zeolite ($Si/Al_2$=90) doped with 3% P; second part 2.5 gm of γ-$Al_2O_3$ doped with 4% Zr; Feed: 0.35 mL/min 92% ethanol, 60 SCCM ethylene, 10 SCCM nitrogen. Regeneration Conditions: Remove catalyst from reactor and place in a static muffle furnace overnight at 500° C. Catalysts were subjected to 24 hours time on stream, then repeatedly regenerated and resubjected to reaction conditions. The data shown in FIG. 4 illustrates ethylene conversion over repeated uses of a phosphor doped zeolite. When comparing the data of FIG. 4 with that the data of FIG. 2, the exemplary cycles with the boron and phosphor doped zeolite (Example 10) are more stable than the exemplary cycles with the phosphor doped zeolite (example 12). As a result, the presence of boron can allow for greater $C_2$ conversion over longer times on stream, which can also provide for more consistent catalytic activity.

What is claimed is:

1. A process for converting one or more $C_1$-$C_5$ linear or branched alcohols to one or more $C_2$-$C_5$ olefins, the process comprising:
    contacting an input stream comprising the one or more $C_1$-$C_5$ linear or branched alcohols with a catalyst in a reactor to form an output stream with greater than about 75 wt % carbon yield, the output stream comprising the one or more $C_2$-$C_5$ olefins, the catalyst consisting essentially of zeolite doped with boron and phosphor;
    wherein the reactor is at a temperature from about 300° C. to about 600° C., a gauge pressure from 0 to about 30 bar, and a weight hourly space velocity (WHSV) from about 0.25 to about 10; and
    wherein boron is present in the catalyst in an amount from about 0.05 wt. % to about 5 wt. %, and wherein phosphor is present in the catalyst in an amount from about 0.2 wt. % to about 7 wt. %.

2. The process of claim 1, wherein the reactor is a single bed reactor.

3. The process of claim 2, wherein the single bed reactor is a fixed bed reactor.

4. The process of claim 2, wherein the single bed reactor is a fluidized bed reactor.

5. The process of claim 2, wherein the single bed reactor is a moving bed reactor.

6. The process of claim 1, wherein the one or more $C_2$-$C_5$ olefins are present in the output stream in an amount that is from about 85 wt. % to about 99 wt. % of the total hydrocarbon products in the output stream.

7. The process of claim 1, wherein the zeolite is a ZSM-5 zeolite.

8. A process for converting one or more $C_1$-$C_5$ linear or branched alcohols to one or more $C_2$-$C_5$ olefins, the process comprising:
    contacting an input stream comprising the one or more $C_1$-$C_5$ linear or branched alcohols with a single catalyst in a reactor to form an output stream with greater than about 75 wt % carbon yield, the output stream comprising the one or more $C_2$-$C_5$ olefins, the single catalyst comprising zeolite doped with boron and phosphor;
    wherein the reactor is at a temperature from about 350° C. to about 750° C., a gauge pressure from 0 to about 30 bar, and a weight hourly space velocity (WHSV) from about 0.25 to about 5; and
    wherein boron is present in the catalyst in an amount from about 0.05 wt. % to about 5 wt. %, and wherein phosphor is present in the catalyst in an amount from about 0.2 wt. % to about 7 wt. %.

9. The process of claim 8, wherein the single catalyst consists essentially of zeolite doped with boron and phosphor.

10. The process of claim 8, wherein the reactor is a single bed reactor.

11. The process of claim 10, wherein the single bed reactor is a fixed bed reactor.

12. The process of claim 10, wherein the single bed reactor is a fluidized bed reactor.

13. The process of claim 10, wherein the single bed reactor is a fluidized bed reactor.

14. The process of claim 8, wherein the one or more $C_2$-$C_5$ olefins are present in the output stream in an amount that is from about 85 wt. % to about 99 wt. % of the total hydrocarbon products in the output stream.

15. The process of claim 8, wherein the zeolite is a ZSM-5 zeolite.

16. A process for converting one or more $C_1$-$C_5$ linear or branched alcohols to one or more $C_2$-$C_5$ olefins, the process comprising:
    contacting an input stream comprising the one or more $C_1$-$C_5$ linear or branched alcohols with a catalyst in a reactor to form an output stream with greater than 85 wt % carbon yield, the output stream comprising the one or more $C_2$-$C_5$ olefins, the catalyst consisting essentially of a ZSM-5 zeolite doped with boron and phosphor;
    wherein the reactor is at a temperature from about 350° C. to about 475° C., a gauge pressure from 0 to about 5 bar, and a weight hourly space velocity (WHSV) from about 0.25 to about 10;

wherein boron is present in the catalyst in an amount from about 0.05 wt. % to about 3 wt. %, and wherein phosphor is present in the catalyst in an amount from about 0.2 wt. % to about 7 wt. %.

\* \* \* \* \*